United States Patent [19]

Schofield et al.

[11] 4,249,015
[45] Feb. 3, 1981

[54] PREPARATION OF ORGANIC ACIDS AND/OR ESTERS

[75] Inventors: John A. Schofield; John E. Hawes, both of Kent, England

[73] Assignee: Shell Oil Company, Houston, Tex.

[21] Appl. No.: 6,975

[22] Filed: Jan. 26, 1979

Related U.S. Application Data

[63] Continuation of Ser. No. 816,572, Jul. 18, 1977, abandoned.

[30] Foreign Application Priority Data

Jul. 23, 1976 [GB] United Kingdom ............... 30817/76

[51] Int. Cl.³ ..................... C07C 67/39; C07C 69/74; C07C 69/76
[52] U.S. Cl. ........................................... 560/1; 560/19; 560/64; 560/67; 560/103; 560/126; 560/128; 560/179; 560/183; 560/187; 560/208; 560/225; 560/265; 562/400; 562/408; 562/433; 562/473; 562/475; 562/508; 562/510; 562/523; 562/579; 562/588; 562/598; 562/493; 562/512; 548/367
[58] Field of Search ..................... 560/1, 55, 208, 236, 560/238, 128, 249, 64, 67, 103, 126, 179, 183, 187, 265; 562/568, 400, 408, 473, 475, 508, 510, 523, 579, 588, 598; 548/367

[56] References Cited

U.S. PATENT DOCUMENTS 2,828,337  3/1958  Whitaker ........................ 260/530 R
3,639,449  2/1972  Kunugi et al. ........................ 560/238

FOREIGN PATENT DOCUMENTS 1331664  9/1973  United Kingdom .

OTHER PUBLICATIONS

Yamane, Yasuhiro et al., "Decarboxylation Reaction of Oxalacetic Acid by Metal Chelates." Chem. Pharm. Bull. 19 (11), 2343–2348, (1971).
Luknitski, F. I., Chemical Reviews (Jun. 1975), 75(3), pp. 259–289.
Bauer, Kurt et al., Ger. Offen., 2,115,551, (See Chemical Abstracts 78 (1973), #3,958q.
Yamane, Yasuhiro et al., Chemical Abstracts 76 (1972), #33,529b.
Mizuguchi, Jun et al., Chemical Abstracts 69 (1968), #102,373r.

*Primary Examiner*—Natalie Trousof
*Assistant Examiner*—L. Hendriksen

[57] ABSTRACT

Carboxylic acids and/or esters are prepared by converting the

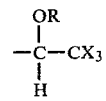

moiety in a 1-substituted 2,2-trihaloethanol, or derivative wherein X represents halogen and R is hydrogen or an acyl group to an organic acid and/or ester grouping of the formula

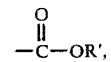

wherein R' is hydrogen or alkyl of 1 to 6 carbon atoms, in the process which comprises reacting the 1-substituted 2,2,2-trihaloethanol or acylated derivative with molecular oxygen in the presence of a catalyst comprising a complex of a transition metal having an atomic number from 21–30, 39–48 or 57–80 and at least one molecule of a ligand containing trivalent nitrogen, phosphorus, arsenic or antimony. This reaction is carried out in a reaction medium comprising an alcohol or aqueous alcohol having 1 to 6 carbon atoms optionally containing an alkali metal, said alcoholic solvent also serving as a reactant source when carboxylic acid esters are formed.

12 Claims, No Drawings

PREPARATION OF ORGANIC ACIDS AND/OR ESTERS

This is a continuation of application Ser. No. 816,572, filed July 18, 1977, now abandoned.

BACKGROUND OF THE INVENTION

This invention relates to a process for the preparation of organic acids and/or esters by transition metal catalyzed oxidation of 1-substituted 2,2,2-trihaloethanols.

Certain 1-aryl-2,2,2-trihaloethanols may be transformed into aldehydes, α-hydroxy acids or keto-alkdehydes by treatment with aqueous or alcoholic alkali. These reactions have been described in, for example, U.K. patent specification 1,331,664 and *Chem. Rev.*, 1975, 75,269,272. A similar pattern of reactivity has been observed with 1-alkenyl-2,2,2-trichloroethanols.

It has now been found that 1-substituted 2,2,2-trihaloethanols or acylated derivatives thereof can be directly converted into carboxylic acids and/or esters by reacting them with molecular oxygen in the presence of a suitable catalyst.

SUMMARY OF THE INVENTION

Accordingly, the present invention provides a process for the preparation of carboxylic acids and/or esters from 1-substituted 2,2,2-trihaloethanols or acylated derivatives thereof which comprises reacting the 1-substituted 2,2,2-trihaloethanol or acylated derivative with molecular oxygen in the presence of a catalyst comprising a transition metal having an atomic number from 21–30, 39–48 or 57–80 complexed with at least one molecule of a ligand containing trivalent nitrogen, phosphorus, arsenic or antimony; thereby converting the

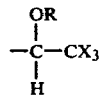

moeity of the 1-substituted 2,2,2-trihaloethanol, wherein X represents halogen and R is hydrogen or an acyl group, to a carboxylic acid and/or ester grouping of the formula

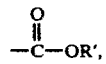

wherein R' represents hydrogen or alkyl of 1 to 6 carbon atoms, said reaction being carried out in an alcohol or aqueous alcohol solvent of the formula R″ OH wherein R″ is alkyl of 1 to 6 carbon atoms, which optionally contains dissolved alkali metal, said alcohol solvent also serving as a source of alcohol reactant for formation of the carboxylic acid esters.

DESCRIPTION OF THE PREFERRED EMBODIMENTS

The term "ligand" as used herein describing the catalysts according to the invention denotes a compound having an element with a pair of electrons capable of forming a coordinate bond with a metal atom and simultaneously having the ability to accept the electrons from the metal, thereby providing additional stability to the resulting complex. Additionally, the term "1-substituted 2,2,2-trihaloethanol" as used herein is intended to denote compounds containing the moietyy

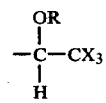

which are both alcohols i.e., R being hydrogen, and acylated derivatives thereof—i.e., R being an acyl group, preferably containing up to 6 carbon atoms—with X being a halogen.

The transition metal which forms part of the complex used as catalyst in the above-described process is preferably copper and the complex preferably contains at least one molecule of a ligand containing trivalent nitrogen, for example 1,10-phenanthroline or 2,2'-bipyridyl. Very good results have been obtained with a complex of copper and two molecules of 1,10-phenanthroline, which complex may be prepared from a salt of copper (for example cupric chloride) and 1,10-phenanthroline.

The amount of catalyst used in the process of the invention preferably is from $10^{-4}$ to 1 equivalents per mole of the 1-substituted 2,2,2-trihaloethanol. However, ratios of catalyst to 1-substituted 2,2,2-trihaloethanol are not particularly critical and may be outside the aforementioned range. In general, large quantities of catalyst will produce a faster reaction rate.

The reaction between the 1-substituted 2,2,2-trihaloethanol and molecular oxygen is suitably carried out in the presence of an alcohol of 1–6 carbon atoms as the reaction solvent, methanol and ethanol being particularly preferred. These alcohol solvents may contain water, preferably in an amount of up to 50% by weight, and optionally contain alkali metal hydroxide or alkoxide. Good yields of the desired end product are obtained if the reaction is carried out under alkaline conditions. A reaction medium consisting of a solution of an alkali metal in an alcohol having 1–6 carbon atoms, for example methanolic sodium methoxide or ethanolic sodium ethoxide, gives excellent results. If the reaction is carried out under alkaline conditions in the presence of an alcohol the end product will normally be an ester. In the presence of an aqueous alcohol the corresponding acid is also formed.

The reaction may suitably be performed at atmospheric pressure but higher or lower pressures may be used if desired. The temperature employed in the reaction will preferably be in the range of 0°–100° C., with temperatures in the range of 15°–50° C. being particularly preferred.

The starting material for the process of the invention may be any suitable 1-substituted 2,2,2-trihaloethanol containing the

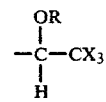

moiety defined above. In this regard, it is preferred that X represents a chlorine atom. The symbol R preferably represents a hydrogen atom but in certain instances R can suitably be an acyl, for example acetyl group. The

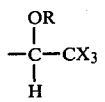

moiety is usually linked to a carbon atom, which preferably is a carbon atom which is part of an aromatic ring or a carbon atom which is attached to one hydrogen atom and three other carbon atoms. For example,

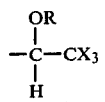

moiety may be linked to an optionally substituted alkyl, alkenyl cycloalkyl, cycloalkenyl or aryl group or to a heterocyclic group containing nitrogen, sulphur and/or oxygen hetero-atoms. In general any of the usual substituents may also be present in the 1-substituted 2,2,2-trichloroethanols e.g., hydroxy and alkoxy groups.

Suitable starting materials include:
(a) 1-(4-methoxyphenyl)-2,2,2-trichloroethanol
(b) 1-(4-ethoxyphenyl)-2,2,2-trichloroethanol
(c) 1-(4-hydroxyphenyl)-2,2,2-trichloroethanol
(d) 1-(4-dimethylaminophenyl)-2,2,2-trichloroethanol
(e) 1-(2-cyclohexen-1-yl)-2,2,2-trichloroethanol
(f) 1-(2-cyclohexen-1-yl)-2,2,2-trichloroethyl acetate
(g) 1-(2,3-dimethyl-1-phenyl-3-pyrazolin-5-one-4-yl)-2,2,2-trichloroethanol
(h) 1,1,1-trichloro-3-methyl-4-penten-2-ol
(i) 1,1,1-trichloro-3-methyl-4-penten-2-yl acetate
(j) 1-cyclohexyl-2,2,2-trichloroethanol
(k) 1-(2-cyclododecen-1-yl)-2,2,2-trichloroethanol
(l) 1-(2-cyclododecen-1-yl)-2,2,2-trichloroethyl acetate
(m) 1-(2-cyclo-octen-1-yl)-2,2,2-trichloroethyl acetate
(n) 1-(2-cyclo-octen-1-yl)-2,2,2-trichloroethanol
(o) 1-(2,4,4-trimethyl-2-cyclohexen-1-yl)-2,2,2-trichloroethyl acetate
(p) 1-(2,4,4-trimethyl-2-cyclohexen-1-yl)-2,2,2-trichloroethanol.

The compounds containing the

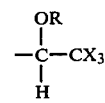

moiety wherein R is a hydrogen atom can easily be obtained from alkylation with chloral in a manner known per se, and can subsequently be acylated to yield compounds wherein R is an acyl group.

The process according to the invention is suitably carried out by combining the 1-substituted 2,2,2-trihaloethanol, with the alcohol solvent, optionally containing dissolved alkali metal and the catalyst and passing a stream of dry oxygen through the combined mixture. Suitably, the oxygen reactant is employed on an approximate equal molar basis with the 1-substituted 2,2,2-trihaloethanol although the use of molar excesses of either reactant is not precluded. The product of the reaction is readily recovered by conventional means i.e. neutralization and extraction. If desired, the esters obtained by the process of the invention can be converted to the corresponding acids by acification.

The compounds obtained by the process of the invention include those which are of value as preservatives and fungistats in food products and flavor compositions or are valuable intermediates for the production of organic compounds useful in the food, cosmetic, aroma chemical, pharmaceutical, agricultural and veterinary fields. Certain methyl esters prepared in accordance with the process of the invention may be transesterfied into valuable aroma chemicals. For instance 1,1,1-trichloro-3-methyl-4-penten-2-ol may be converted into methyl tiglate which may subsequently be transesterified with geraniol.

If the starting material is an optionally substituted 1-(2-alken-1-yl)- or 1-(2-cycloalken-1-yl)-2,2,2-trihaloethanol the oxidation reaction may yield a mixture of the α,β-unsaturated and the β,γ-unsaturated acid or ester as shown in the following scheme:

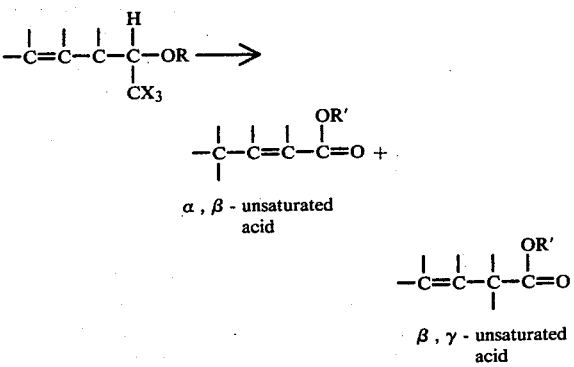

This mixture can be converted entirely into the α,β-unsaturated acid or ester by base catalyzed isomerization of the β,γ-unsaturated acid or ester using conventional methods.

Compounds prepared in accordance with the process of the invention include the following novel compounds:
geranyl cyclohexane carboxylate
methyl 2,4,4-trimethyl-2-cyclohexene-1-carboxylate
2,4,4-trimethyl-2-cyclohexene-1-carboxylic acid
methyl 2-cyclododecene-1-carboxylate
methyl 1-cyclododecene-1-carboxylate Sometimes, for example in the case of oxidation of 1,1,1-trichloro-3-methyl-4-penten-2-ol to methyl tiglate, only the α-β-unsaturated ester or acid is obtained. In other cases, however, the β-Γ-unsaturated acid or ester is the major product.

The process of the invention is further illustrated in the following Examples.

EXAMPLE 1

Preparation of methyl 4-methoxybenzoate

Cupric chloride dihydrate (0.125 g; 0.733 m. moles) and 1,10-phenanthroline hydrate (0.375 g; 1.9 m. moles) were added to a solution of sodium (1.15 g; 50 m. moles) in methanol (75 ml) and a steam of dry oxygen was passed through the stirred mixture. 1-(4-Methoxyphenyl)-2,2,2-trichloroethanol (11.1 g; 43.5 m. moles) was added and the mixture heated (bath temp. 30°–35° C.) for a period of 1 hour. The reaction mixture was then diluted with water, acidified with hydrochloric acid and extracted with ether (3×50 ml). The combined ether extracts were washed with dilute aqueous sodium carbonate and water, dried (MgSO$_4$) and evaporated. The residue was distilled to give methyl 4-methoxybenzoate (6.5 g; yield 96%), b.p. 134°-135° C./12 mm, m.p. 45°-45° C.

Analysis: Calculated for C$_9$H$_{10}$O$_3$: C 65.05; H 6.1%. Found: C 64.9; H 6.0%

The product had a purity of 99.6% as determined by G.L.C.

EXAMPLE 2

Preparation of methyl 4-methoxybenzoate and 4-methoxybenzoic acid

A stream of oxygen was passed through a stirred solution of 1-(4-methoxyphenyl)-2,2,2-trichloroethanol (5.1 g; 20 m. moles) in a mixture of water (43.2 ml) and methanol (40 ml) and a solution of cupric chloride dihydrate (0.05 g; 0.29 m. mole), 1,10-phenanthroline hydrate (0.15 g; 0.76 m. mol) and sodium hydroxide (1.6 g; 40 m. moles) in methanol (20 ml) was added over a period of 15 minutes. The reaction was allowed to continue for a further 3 hours at a temperature of 20°-25° C. after which a solution of cupric chloride dihydrate (0.01 g; 0.06 m. mole) and 1,10-phenanthroline hydrate (0.03 g; 0.15 m. mole) in methanol (2 ml) was added.

After a total of 6¾ hours reaction time, the mixture was diluted with dilute hydrochloric acid, saturated with sodium chloride and extracted four times with ether. The combined extracts were washed twice with aqueous sodium carbonate solution, dried (MgSO$_4$) and evaporated to give methyl 4-methoxybenzoate (1.44 g; yield 43%; 98% purity as indicated by G.L.C.), m.p. 41°-47° C. The product was further distilled to give material (1.3 g; yield 39%), b.p. 134°-135° C./12 mm, m.p. 44°-46° C.

The combined sodium carbonate extracts were acidified, saturated with sodium chloride and extracted four times with ether. The combined, dried (MgSO$_4$) extracts were evaporated and the residue recrystallised from water to give 4-methoxybenzoic acid (0.95 g; yield 31%), m.p. 181°-185° C.

EXAMPLE 3

Preparation of methyl 4-ethoxybenzoate

Cupric chloride dihydrate (0.125 g; 0.733 m. moles) and 1,10-phenanthroline hydrate (0.375 g; 1.9 m. moles) were added to a solution of sodium (1.15 g; 50 m. moles) in methanol (75 ml). A stream of dry oxygen was passed through the mixture, 1-(4-ethoxyphenyl)-2,2,2-trichloroethanol (11.72 g; 43.6 m. moles) added and the mixture stirred at 30°-35° C. for 1 hour. The reaction mixture was diluted with water (200 ml), acidified with hydrochloric acid and extracted with ether (3×50 ml). The combined ether extracts were washed with dilute aqueous sodium carbonate and water, dried (MgSO$_4$) and evaporated. The residue was distilled to give methyl 4-ethoxybenzoate (7.5 g; yield 88%), b.p. 142°-143° C./12 mm, m.p. 35°-37° C.

Analysis: Calculated for C$_{10}$H$_{12}$O$_3$: C 66.65; H 6.7%. Found: C 66.9; H 6.7%.

The product had a purity of 99% as determined by G.L.C.

EXAMPLE 4

Preparation of methyl 4-ethoxybenzoate

Cupric chloride dihydrate (0.064 g; 0.38 m. mole) and 2,2'-bipyridyl (0.15 g; 0.96 m. mole) were added to a solution of sodium (0.582 g; 25.3 m. moles) in methanol (42 ml) and a stream of dry oxygen was passed through the stirred mixture. 1-(4-Ethoxyphenyl)-2,2,2-trichloroethanol (6.9 g; 25.4 m. moles) was added and the mixture heated (bath temp. 30°-25° C.) for a period of 1¼ hours. The reaction mixture was then diluted with water (100 ml), acidified with hydrochloric acid and extracted with ether (3×50 ml). The combined ether extracts were washed with saturated aqueous sodium carbonate (50 ml) and water (50 ml), dried (MgSO$_5$) and evaporated. The residue was distilled to give methyl 4-ethoxybenzoate (4.05 g; 88%), b.p. 143° C./12 mm.

EXAMPLE 5

Preparation of ethyl 4-ethoxybenzoate

Cupric chloride dihydrate (0.125 g; 0.733 m. moles) and 1,10-phenanthroline hydrate (0.375 g; 1.9 m. moles) were added to a solution of sodium (1.15 g; 50 m. moles) in ethanol (75 ml). A stream of dry oxygen was passed through the mixture, 1-(4-ethoxyphenyl)-2,2,2-trichloroethanol (11.72 g; 43.6 m. moles) added and the mixture stirred at 30°-35° C. for 1½ hours. A solution of sodium (0.575 g; 25 m. moles) in ethanol (10 ml) was then added and the reaction was allowed to continue for a further 1 hour. The reaction mixture was diluted with water (250 ml), acidified with hydrochloric acid and extracted with ether (3×50 ml). The combined ether extracts were washed once with water and twice with dilute aqueous sodium carbonate, dried (MgSO$_4$) and evaporated. The residue was distilled to give ethyl 4-ethoxybenzoate (5.3 g; yield 66%), b.p. 148°-150° C./12 mm.

Analysis: Calculated for C$_{11}$H$_{14}$O$_3$: C 68.0; H 7.3%. Found: C 68.0; H 7.3%.

The product had a purity of 97-98% as determined by G.L.C.

EXAMPLE 6

Preparation of methyl 4-hydroxybenzoate

A stream of dry oxygen was passed through a solution of 1-(4-hydroxyphenyl)-2,2,2-trichloroethanol (2.41 g; 10 m. moles) in methanol (10 ml) and a solution of sodium (0.48 g; 20.9 m. moles) in methanol (10 ml) containing cupric chloride dihydrate (0.025 g; 0.15 m. moles) and 1,10-phenanthroline hydrate (0.075 g; 0.38 m. moles) was added portionwise over a period of 50 minutes. The reaction mixture was maintained at a temperature of 20°-25° C. and the reaction was allowed to continue for a further 2 hours and the reaction mixture was then poured into dilute hydrochloric acid, extracted with ether (3×25 ml) and the combined ether extracts washed twice with water. The dried (MgSO$_4$) extract was evaporated to dryness and the residue crystallised from aqueous ethanol to give methyl 4-hydroxybenzoate (1.0 g; yield 66%), m.p. 124°-126° C. A sample was recrystallised for analysis from a mixture of carbon tetrachloride and a chloroform to give material of m.p. 126°-131° C.

Analysis: Calculated for C$_8$H$_8$O$_3$: C 63.15; H 5.3%. Found: C 63.2; H 5.4%.

EXAMPLE 7

Preparation of methyl 4-dimethylaminobenzoate

A stream of dry oxygen was passed through a solution (heated at 30° C.) of 1-(4-dimethylaminophenyl)-2,2,2-trichloroethanol (5.37 g; 20 m. moles) in methanol (50 ml) and a solution of cupric chloride dihydrate (0.05 g; 0.29 m. mole) and 1,10-phenanthroline hydrate (0.15 g; 0.76 m. mole) in methanol (50 ml) in which sodium (0.5 g; 21.7 m. moles) had been dissolved was added portionwise over a period of 1¼ hours.

The reaction mixture was diluted with water (200 ml), extracted with ether (3×50 ml) and the combined extracts washed with water. The dried (MgSO$_4$) extract was evaporated to give a pale yellow solid (3.75 g) which was recrystallised from aqueous methanol to give methyl 4-dimethylaminobenzoate (2.7 g; 75%), m.p. 98°–99° C.

Analysis: Calculated for $C_{10}H_{13}NO_2$: C 67.0; H 7.3; N 7.8%. Found: C 66.8; H 7.6; N 7.6%.

EXAMPLE 8

(a) Preparation of 1-(2-cyclohexen-1-yl)-2,2,2-trichloroethanol

Anhydrous aluminum chloride (8.4 g; 0.063 mole) was added portionwise over a period of 2 hours to a stirred mixture of cyclohexene (108 g; 1.32 moles) and chloral (97 g; 0.653 mole), the temperature of which was maintained at 0° C. The reaction was allowed to proceed for a further 1 hour at 0° C. and then poured into a mixture of ice and concentrated hydrochloric acid. The reaction mixture was extracted three times with ether and the combined extracts washed with water (2×200 ml). The dried (MgSO$_4$) extract was evaporated and the residue distilled to give crude product (116 g; 85% purity as judged by G.L.C.), b.p. 90°–94° C./0.1 mm. The crude product was redistilled through a Widmer column to give 1-(2-cyclohexen-1-yl)-2,2,2-trichloroethanol (98 g; 65% yield based on chloral; 93% purity as judged by G.L.C.) b.p. 67°–68° C./0.03 mm. A sample was redistilled for analysis.

Analysis: Calculated for $C_8H_{11}Cl_3O$: C 46.4; H 4.8; Cl 42.0%. Found: C 46.0; H 4.8; Cl 41.8%.

(b) Preparation of methyl 2-cyclohexene-1-carboxylate 1-(2-Cyclohexen-1-yl)-2,2,2-trichloroethanol (20 g; 87.3 m. moles) was added to a solution of cupric chloride dihydrate (0.25 g; 1.47 m. moles) and a 1,10-phenanthroline hydrate (0.75 g; 3.8 m. moles) in methanol (150 ml). A rapid stream of oxygen was passed through the vigorously stirred solution and a solution of sodium (2.5 g; 108.5 m. moles) in methanol (50 ml) was added over a period of 4¼ hours. A solution of cupric chloride dihydrate (0.125 g; 0.733 m. moles) and 1,10-phenanthroline hydrate (0.375 g; 1.9 m. moles) in methanol (10 ml) was then added and the reaction allowed to proceed for a further 1¼ hours at a temperature of 20°–25° C. The reaction mixture was poured into ice-cold dilute hydrochloric acid, extracted with ether (4×100 ml) and the combined extracts washed twice with dilute aqueous sodium carbonate. The dried (MgSO$_4$) extract was evaporated and the residue distilled to give a mixture of methyl 2-cyclohexene-1-carboxylate and methyl 1-cyclohexene-1-carboxylate (7.2 g; yield 59%), b.p. 80°–85° C./12 mm, containing about 90% of the former as indicated by G.L.C.

Analysis: Calculated for $C_8H_{12}O_2$: C 68.5; H 8.6%. Found: C 68.1; H 8.7%.

The product was purified further by distillation through a spinning band column to give methyl 2-cyclohexen-1-carboxylate, b.p. 179° C./755 mm (N.M.R.: δ5.7 (s,2,CH=CH), 3.6 (s,3,OCH$_3$), 2.79–3.18 (m,1,tertiary), 1.5–2.2 (m,6,CH$_2$CH$_2$CH$_2$)).

Analysis: Calculated for $C_8H_{12}O_2$: C 68.5; H 8.6%. Found: C 68.8; H 8.9%.

(c) Preparation of methyl-1-cyclohexene-1-carboxylate

Methyl 2-cyclohexene-1-carboxylate (4.0 g; 28.5 m. moles) was added to a solution of sodium (0.73 g; 31.7 m. moles) in methanol (20 ml) and the mixture was allowed to stand at room temperature for a period of 2½ hours. The mixture was poured into dilute hydrochloric acid, extracted with ether (4×25 ml) and the combined extracts washed with dilute aqueous sodium carbonate and then water. The dried (MgSO$_4$) extract was evaporated and the residue distilled to give methyl 1-cyclohexene-1-carboxylate (3.5 g; yield 87.5%), b.p. 84° C./15 mm.

Analysis: Calculated for $C_8H_{12}O_2$: C 68.5; H 8.6%. Found: C 68.3; H 9.0%.

The product was purified further by distillation through a spinning band column to give material, b.p. 193° C./755 mm (N.M.R.: δ6.85–6.9 (m,1, CH=C), 3.65 (s,3,OCH$_3$), 2.0–2.4 (m,4, allylic CH$_2$), 1.45–1.88 (m,4,CH$_2$—CH$_2$)).

(d) Preparation of ethyl 1-cyclohexene-1-carboxylate

Methyl 2-cyclohexene-1-carboxylate (5.6 g; 40 m. moles) was added to a solution of sodium (1.1 g; 47.8 m. moles) in ethanol (35 ml) and the mixture was allowed to stand at room temperature for a period of 1½ hours. The mixture was poured into dilute hydrochloric acid extracted with ether (4×25 ml) and the combined extracts washed with dilute aqueous sodium carbonate. The dried (MgSO$_4$) extract was evaporated and the residue distilled to give ethyl 1-cyclohexene-1-carboxylate (5.5 g; yield 90%), b.p. 92° C./15 mm (N.M.R.: 6.7–7.0 (m,1,CH=C), 3.9–4.25 (q,2,$\underline{CH_2}$CH$_3$), 1.95–2.42 (m,4,allylic CH$_2$), 1.13–1.42 (t,3,$\overline{CH_2}\underline{CH_3}$) 1.45–1.92 (m,4,CH$_2$—CH$_2$)).

Analysis: Calculated for $C_9H_{14}O_2$: C 70.1; H 9.15%. Found: C 69.6; H 9.1%.

EXAMPLE 9

Preparation of methyl 2,3-dimethyl-1-phenyl-3-pyrazolin-5-one-4-carboxylate

A stream of dry oxygen was passed through a stirred suspension heated at 30° C.) of 1-(2,3-dimethyl-1-phenyl-3-pyrazolin-5-one-4-yl)-2,2,2-trichloroethanol (3,35 g; 10 m. moles) in methanol (15 ml) and a solution of cupric chloride dihydrate (0.025 g; 0.15 m. mole) and 1,10-phenanthroline hydrate 0.075 g; 0.38 m. mole) in methanol (15 ml) in which sodium (0.27 g; 11.7 m. moles) had been dissolved was added portionwise over a period of 60 minutes. The reaction was allowed to proceed for a further 60 minutes, the reaction mixture diluted with dilute sulphuric acid and adjusted to pH 6.0–6.5 by addition of aqueous sodium bicarbonate. The mixture was extracted with chloroform (3×50 ml), the combined extracts washed with saturated aqueous sodium carbonate (10 ml), dried (MgSO$_4$) and evaporated to give methyl 2,3-dimethyl-1-phenyl-3-pyrazolin-5-one-4-carboxylate (2.15 g; 87%). The product was recrystallised from acetone to give material, m.p. 154°–157° C.

Analysis: Calculated for $C_{13}H_{14}N_2O_3$: C 63.4; H 5.7; N 11.4%. Found: C 63.6; H 5.8; N 11.2%.

EXAMPLE 10

(a) Preparation of 1,1,1-trichloro-3-methyl-4-penten-2-yl acetate

Anhydrous aluminum chloride (5.3 g; 0.039 mole) was added portionwise over a period of 45 minutes to a stirred and cooled (−5° C. to −10° C.) solution of cis 2-butene (44 g; 0.786 mole) and chloral (57 g; 0.388 mole) in light petroleum (b.p. 40°-60° C.; 100 ml). The reaction mixture was stirred at −5° C. to −10° C. for a further 30 minutes, poured into a mixture of ice and concentrated hydrochloric acid and the light petroleum layer separated. The aqueous phase was extracted with ether (2×100 ml) and the combined ether and light petroleum extracts washed with dilute aqueous sodium carbonate and water. The dried (MgSO$_4$) extract was evaporated and the residue (83 g) distilled to give the crude chloral adduct (60.5 g), b.p. 88°-95° C./12 mm.

The crude adduct was dissolved in acetic anhydride (150 ml), the solution refluxed for 4 hours and then allowed to stand overnight at room temperature. Acetic acid and anhydride were removed by distillation through a Widmer column and the residue was distilled through a spinning band column to give 1,1,1-trichloro-3-methyl-4-penten-2-yl acetate (39 g; 41% yield based on chloral; 99.6% purity as judged by G.L.C.), b.p. 99.5°-100° C./15 mm.

(b) Preparation of methyl tiglate

A rapid stream of oxygen was passed through a vigorously stirred solution of 1,1,1-trichloro-3-methyl-4-penten-2-ol (13 g; 64 m. moles) in methanol (100 ml) and a mixture of cupric chloride dihydrate (0.325 g; 1.91 m. moles), 1,10-phenanthroline hydrate (0.975 g; 4.92 m. moles) and a solution of sodium (3.2 g; 140 m. moles) in methanol (100 ml) was added over a period of 1¾ hours at a temperature of 20°-25° C. The reaction was allowed to proceed for a further ½ hour and the reaction mixture was then poured into dilute hydrochloric acid, extracted with ether (4×75 ml) and the combined extracts washed with dilute aqueous sodium carbonate. The dried (MgSO$_4$) extract was evaporated and the residue was twice distilled through a fractionating column to give methyl tiglate (4.7 g; yield 64%), b.p. 139°-140° C./760 mm (N.M.R.: 6.75 (m,1,CH=C), 3.64 (s,3,COOCH$_3$), 1.77 (d,3,$\underline{CH_3}$-CH), 1.8 (s,3,CH$_3$-C)). The material was identical with a sample obtained by direct esterification of tiglic acid.

(c) Preparation of geranyl tiglate

A 50% oil suspension of sodium hydride (3.0 g; 62.5 m. moles) was washed twice with light petroleum (b.p. 60°-80° C.) and geraniol (25 ml) was added. The mixture was maintained at room temperature by external cooling until reaction had ceased and the further cooled to 20° C. Methyl tiglate (3.42 g; 30 m. moles) was added over a period of 10 minutes, the temperature being maintained at 25° C. and the reaction mixture was finally stirred at room temperature for a further 60 minutes.

The mixture was poured into dilute hydrochloric acid, extracted four times with ether and the combined extracts washed with aqueous sodium carbonate solution. The dried (MgSO$_4$) extract was evaporated, excess geraniol removed by distillation and the residue distilled to give geranyl tiglate (4.1 g; yield 58.5%, 90% purity as indicated by G.L.C.), b.p. 88°-90° C./0.01 mm.

The product was redistilled for analysis to give material (97% purity as indicated by G.L.C.), b.p. 88° C./0.05 mm.

Analysis: Calculated for C$_{15}$H$_{24}$O$_2$: C 76.2; H 10.2%. Found: C 76.5; H 10.5%.

EXAMPLE 11

(a) Preparation of 1-cyclohexyl-2,2,2-trichloroethanol

Adam's catalyst (0.2 g) was added to a solution of 1-(2-cyclohexen-1-yl)-2,2,2-trichloroethanol (23 g) in methanol (220 ml) and this mixture was stirred under a slight positive pressure of hydrogen. Uptake of hydrogen was complete after 400 minutes and the solution was then filtered. The filtrate was evaporated to give 1-cyclohexyl-2,2,2-trichloroethanol of 90% purity as judged by G.L.C. An attempt to purify this material by distillation through a spinning band column gave material of only 85% purity due, presumably, to decomposition brought about by prolonged heating. This material was used without further treatment.

(b) Preparation of methyl cyclohexanecarboxylate

A rapid stream of oxygen was passed through a stirred solution of 1-cyclohexyl-2,2,2-trichloroethanol (12 g; 85% purity) in methanol (100 ml) and a mixture of cupric chloride dihydrate (0.125 g; 0.735 m. moles) and 1,10-phenanthroline hydrate (0.375 g; 1.89 m. moles) in a solution of sodium (1.31 g; 57 m. moles) in methanol (50 ml) was added portionwise over a period of 90 minutes at a temperature of 20°-25° C. The reaction was continued for a further 90 minutes and the reaction mixture was then diluted with dilute hydrochloric acid and extracted with ether (4×50 ml). Solvent was removed from the combined dried (MgSO$_4$) extracts by distillation through a Widmer column and the residue distilled to give methyl cyclohexane carboxylate (5.05 g; 81% yield), b.p. 75°-80° C./15 mm (98-99% purity). The material was identical with a sample obtained by direct esterification of cyclohexanecarboxylic acid.

(c) Preparation of geranyl cyclohexanecarboxylate

Sodium hydride (1.0 g of a 50% oil dispersion) was twice washed with light petroleum and geraniol (9 ml) was added portionwise, with cooling, over a period of 2 minutes. When the vigorous reaction had subsided, methyl cyclohexane-carboxylate (1.42 g) was added and the mixture stirred at room temperature for a period of 90 minutes. The mixture was added to dilute hydrochloric acid, extracted three times with ether and the combined extracts were washed with aqueous sodium carbonate solution. The dried (MgSO$_4$) extract was evaporated and the residue distilled to give a fore-run of geraniol and then geranyl cyclohexanecarboxylate (1.75 g; 66%), b.p. 120° C./0.1 mm.

Analysis:

Calculated for C$_{17}$H$_{28}$O$_2$: C 77.2; H 10.7%. Found: C 77.2; H 10.7%.

EXAMPLE 12

(a) Preparation of methyl 2-cyclododecene-1-carboxylate

Aluminum chloride (6.65 g; 0.05 mole) was added portionwise over a period of 1 hour to a stirred and cooled (0° C.) mixture of cyclododecene (83 g; 0.5 mole) and chloral (37 g; 0.25 mole). The temperature of the reaction mixture was then allowed to rise to room temperature over a period of 1 hour and the mixture was then stirred for 7 hours, poured into dilute hydrochloric acid and extracted three times with ether. The combined extracts were washed twice with aqueous sodium carbonate solution, dried (MgSO$_4$) and solvent then removed by distillation. The remainder was distilled to give unchanged cyclododecene (34.5 g; yield 42%), b.p. 60°-70° C./0.05 mm.

A stream of dry oxygen was passed through a stirred solution of the distillation residue (73 g) in methanol (450 ml) and a solution of cupric chloride dihydrate (0.5 g; 2.93 m. moles), 1,10-phenanthroline hydrate (1.5 g; 7.6 m. moles) and sodium (5.9 g; 256 m. moles) in methanol (100 ml) was added portionwise over a period of 2.5 hours at a temperature of 20°–25° C. The reaction was continued for a further 1 hour and the reaction mixture then diluted with dilute hydrochloric acid and extracted four times with ether. The combined extracts were washed with aqueous sodium carbonate solution, dried (MgSO$_4$), evaporated and the residue distilled to give methyl 2-cyclododecene-1-carboxylate (35 g; 62.5% yield based on chloral), b.p. 90°–150° C./0.1 mm. G.L.C. indicated a purity of 81%.

A sample was distilled for analysis through a spinning band column to give material, b.p. 99.102° C./0.05 mm (N.M.R.: δ5.3–5.54 (m,2,CH=CH), 3.58 (s,3,OCH$_3$), 2.58–3.05 (m,1,tertiary), 0.96–2.5 (m,16,—(CH$_2$)$_8$).

Analysis: Calculated for C$_{14}$H$_{24}$O$_2$: C 74.95; H 10.8%. Found: C 74.8; H 10.9%.

(b) Preparation of methyl 1-cyclododecene-1-carboxylate

Methyl 2-cyclododecene-1-carboxylate (7.75 g; 34.6 m. moles, 85% purity as shown by G.L.C.), was added to a solution of sodium (0.9 g; 39 m. moles) in methanol (50 ml) and the mixture was allowed to stand at 50° C. for 8 hours and then at room temperature for a further 16 hours. The reaction mixture was diluted with dilute hydrochloric acid, extracted four times with ether and the combined extracts washed with dilute sodium carbonate solution. The dried (MgSO$_4$) extract was evaporated to give methyl 1-cyclododecene-1-carboxylate (7.0 g; 85% purity as shown by G.L.C.). This corresponds to a yield of 90%.

A sample was distilled for analysis through a spinning band column to give material, b.p. 120° C./0.3 mm (N.M.R.: δ6.45–6.83 (t,1,CH=C), 3.65 (s,3,OCH$_3$), 0.7–2.55 (m,20,—(CH$_2$)$_{10}$—).

Analysis: Calculated for C$_{14}$H$_{24}$O$_2$: C 74.95; H 10.8%. Found: C 74.6; H 10.9%.

(c) Preparation of 1-(2-cyclododecen-1-yl)-2,2,2-trichloroethyl acetate

A stirred mixture of cyclododecene (83 g; 0.5 mole) and chloral (37 g; 0.25 mole) was cooled to 0° C. and anhydrous aluminum chloride (6.65 g; 0.05 mole) was added portionwise over a period of 1¼ hours. The mixture was then stirred for a further 8 hours at room temperature, poured into ice-cold dilute hydrochloric acid and extracted three times with ether. The combined extracts were washed twice with aqueous sodium carbonate solution, dried (MgSO$_4$) and evaporated. Distillation yielded unchanged cyclododecene (34.5 g; 42%), b.p. <60° C./0.05 mm, and a residue (73 g) of crude chloral adduct.

The crude adduct was diluted with acetic anhydride (150 ml) and the solution heated under reflux for 5 hours and then allowed to stand overnight at room temperature. Acetic acid and anhydride were removed by distillation and the residue was distilled to give 1-(2-cyclododecen-1-yl)-2,2,2-trichloroethyl acetate (47 g; 53% yield based on chloral; 95% purity as judged by G.L.C.),, b.p. 133°–135° C./0.01 mm.

Analysis: Calculated for C$_{16}$H$_{25}$Cl$_3$O$_2$: C 54.0; H 7.0; Cl 30.0%. Found: C 54.2; H 7.4; Cl 29.7%.

(d) Preparation of methyl 2-cyclododecene-1-carboxylate

A stream of dry oxygen was passed through a stirred solution (heated at 30°–35° C.) of 1-(2-cyclododecen-1-yl)-2,2,2-trichloroethyl acetate (12 g; 35 m. moles) in methanol (10 ml) and a solution of cupric chloride dihydrate (0.19 g; 1.1 m. moles) and 1,10-phenanthroline hydrate (0.56 g; 2.85 m. moles) in methanol (45 ml) in which sodium (1.39 g; 6.0 m. moles) had been dissolved was added portionwise over a period of 225 minutes. The mixture was then diluted with dilute hydrochloric acid (100 ml), extracted with ether (3×50 ml) and the combined ether extracts were washed with aqueous sodium carbonate solution (50 ml) and water (50 ml). The dried (MgSO$_4$) extract was evaporated and the crude product (4.7 g) distilled to give methyl 2-cyclododecene-1-carboxylate (3.9 g; 56%), b.p. 90°–110° C./0.1 mm. G.L.C. analysis indicated a purity of 85%.

EXAMPLE 13

(a) Preparation of 1-(2-cyclo-octen-1-yl)-2,2,2-trichloroethyl acetate

A solution of cyclo-octene (28 g; 0.254 mole) and chloral (35 g; 0.244 mole) in light petroleum (b.p. 80°–100° C.; 200 ml) was cooled to −70° C., anhydrous aluminum chloride (4.0 g; 0.03 mole) added and the mixture stirred for a period of 1 hour. The cooling bath was then removed and the mixture stirred at room temperature for a further 3¼ hours. The reaction mixture was poured on to a mixture of ice (150 g) and concentrated hydrochloric acid (50 ml), the light petroleum phase separated and the aqueous phase extracted with light petroleum (b.p. 80°–100° C.; 2×40 ml). The combined extracts were washed with saturated aqueous sodium carbonate (2×100 ml) and water (100 ml) then dried (MgSO$_4$) and evaporated to give the crude chloral adduct (71.2 g).

A portion (40 g) of the crude adduct was dissolved in acetic anhydride (75 ml) and the solution was heated under reflux for a period of 18 hours and then allowed to stand overnight at room temperature. Acetic acid and anhydride were removed by distillation and the residue was distilled to give the crude product (27 g; 85% purity as judged by G.L.C.), b.p. 100°–110° C./0.03 mm. Fractional distillation gave 1-(2-cyclo-octen-1-yl)-2,2,2-trichloroethyl acetate (22 g; 54% based on choral; 95% purity as judged by G.L.C.), b.p. 100°–102° C./0.05 mm.

Analysis Calculated for C$_{12}$H$_{17}$Cl$_3$O$_2$:C 48.1; H 5.7; Cl 33.55%. Found: C 48.5; H 5.6; Cl 35.8%.

(b) Preparation of methyl 2-cyclooctene-1-carboxylate

A solution of cyclooctene (28 g; 254 m. moles) and chloral (36 g; 244 m. moles) in light petroleum (b.p. 80°–100° C.; 200 ml) was stirred and cooled and aluminum chloride (4 g; 30 m. moles) was added. The reaction was allowed to proceed for a period of 1 hour and was then stirred at room temperature for a further 3½ hours. Ice (150 g) and concentrated hydrochloric acid (50 ml) was added, the mixture extracted with light petroleum (b.p. 40°–60° C.; 2×400 ml) and the combined extracts washed with saturated aqueous sodium carbonate (2×100 ml) and water (100 ml). The dried (Na$_2$SO$_4$) extract was evaporated to give crude 1-(2-cycloocten-1-yl)-2,2,2-trichloroethanol (61.4 g) as a brown oil.

A stream of dry oxygen was passed through a heated (30° C.) solution of the crude product (25 g) in methanol (150 ml) and a solution of cupric chloride dihydrate (0.36 g; 2.12 m. moles) and 1,10-phenanthroline hydrate (1.1 g; 5.55 m. moles) in methanol (180 ml) in which sodium 3.6 g; 157 m. moles) had been dissolved was added portionwise over a period of 85 minutes. The reaction was allowed to proceed for a further 15 minutes, the reaction mixture poured into a mixture of ice (150 g) and concentrated hydrochloric acid and extracted with light petroleum (b.p. 40°–60° C.; 2×300 ml). The combined extracts were washed with saturated aqueous sodium bicarbonate (2×200 ml) and water (200 ml). The dried (Na$_2$SO$_4$) extract was evaporated and the residue distilled through a Vigreux column to give a mixture (5.9 g; 35% based on chloral), b.p. 108°–113° C./12 mm, of methyl 2-cyclooctene-1-carboxylate (79% as judged by G.L.C.) and methyl 1-cyclooctene-1-carboxylate (15% as judged by G.L.C.). A sample of the mixed esters was redistilled for analysis to give material, b.p. 114° C./12 mm.

Analysis Calculated for C$_{10}$H$_{16}$O$_2$: C 71.4; H 9.5%. Found: C 71.4; H 9.6%.

A sample (28.3 g; 74%–17% composition) of the mixed esters was distilled through a spinning band column to give methyl 2-cyclooctene-1-carboxylate (14.4 g; 99.4% pure as judged by G.L.C.), b.p. 114°–116° C./23 mm (N.M.R.: δ5.5–5.8 (m,2,CH=CH), 3.61 (s,3,OCH$_3$), 3.0–3.5 (m,1,tertiary), 0.8–2.6 (m,10,—(CH$_2$)$_5$—)).

(c) Preparation of methyl 1-cyclooctene-1-carboxylate

A sample (6.9 g; 41 m. moles) of mixed esters containing methyl 2-cyclooctene-1-carboxylate (61%) and methyl 1-cyclooctene-1-carboxylate (39%) was added to a solution of sodium (1.0 g; 43 m. moles) in methanol (50 ml), the mixture stirred for 6 hours at room temperature and then allowed to stand overnight. The solution was poured on to a mixture of ice (100 g) and concentrated hydrochloric acid (150 ml), extracted with light petroleum (b.p. 40°–60° C.; 2×150 ml) and the combined extracts were washed with saturated aqueous sodium bicarbonate (2×100 ml) and water (100 ml). The dried (Na$_2$SO$_4$) extract was evaporated and the residue distilled to give methyl 1-cyclooctene-1-carboxylate (4.4 g; 64%, 99% pure as judged by G.L.C.), b.p. 118°–119° C./14 mm, (N.M.R.: δ6.7–6.95 (t,1,CH=C), 3.63 (s,3,OCH$_3$), 1.9–2.7 (m,4,allylic CH$_2$), 1.2–1.85 (m,8,—(CH$_2$)$_4$—)).

Analysis: Calculated for C$_{10}$H$_{16}$O$_2$: C 71.4; H 9.5%. Found: C 71.5; H 9.6%.

EXAMPLE 14

(a) Preparation of 1-(2,4,4-trimethyl-2-cyclohexen-1-yl)-2,2,2-trichloroethyl acetate Anhydrous aluminum chloride (0.95 g; 7.14 m. moles) was added to a stirred and cooled (0° C.) mixture of chloral (6.6 ml; 68.2 m. moles) and cyclogeraniolene (6.7 g; 54 m. moles) and the mixture allowed to warm up to room temperature over a period of 1 hour. The reaction mixture was then stirred for a period of 30 minutes at room temperature, chloral (0.75 ml; 7.75 m. moles) and aluminum chloride (0.1 g; 0.75 m. mole) added and the reaction allowed to proceed for a further 1 hour. The reaction mixture was poured into dilute hydrochloric acid, extracted three times with ether and the combined ether extracts washed with aqueous sodium carbonate solution. The dried (MgSO$_4$) extract was evaporated and the residue distilled to give crude chloral adduct (8.5 g; 58% yield based on cyclogeraniolene) b.p. 105°–110° C./0.8 mm.

A portion (1 g) of the crude product was dissolved in acetic anhydride (10 ml) and the solution heated under reflux for 72 hours. The solution was diluted with water, extracted three times with ether and the combined extracts washed twice with water. The dried (MgSO$_4$) extract was evaporated and the residue flash distilled under reduced pressure (0.5 mm) to give 1-(2,4,4-trimethyl-2-cyclohexen-1-yl)-2,2,2-trichloroethyl acetate (0.9 g; 45% yield based on cyclogeraniolene).

Analysis: Calculated for C$_{13}$H$_{19}$Cl$_3$O$_2$: C 49.8; H 6.1%. Found: C 49.8; H 6.1%.

(b) Preparation of methyl 2,4,4-trimethyl-2-cyclohexane-1-carboxylate

A stream of dry oxygen was passed through a heated (30° C.) solution of 1-(2,4,4-trimethyl-2-cyclohexen-1-yl)-2,2,2-trichloroethanol (5.8 g; 21.5 m. moles) in methanol (20 ml) and a solution of cupric chloride dihydrate (0.08 g; 0.47 m. mole) and 1,10-phenanthroline hydrate (0.24 g; 1.2 m. moles) in methanol (32 ml) in which sodium (0.96 g; 41.7 m. moles) had been dissolved was added over a period of 6½ hours. The reaction mixture was poured into dilute hydrochloric acid, extracted with ether and the extract washed with aqueous sodium carbonate. The dried (MgSO$_4$) extract was evaporated and the residue distilled to give methyl 2,4,4-trimethyl-2-cyclohexane-1-carboxylate (2.4 g; 61%), b.p. 99°–100° C./12 mm. (N.M.R. : δ0.93 (s,3,CH$_3$—C—CH$_3$), 0.99 (s,3,CH$_3$—C—CH$_3$), 1.62 (d,J=~1 Hz. 3, C=C—CH$_3$), 5.16–5.3 (m,1,C=CH), 3.61 (s,1,OCH$_3$)).

Analysis: Calculated for C$_{11}$H$_{18}$O$_2$: C 72.5; H 10.0%. Found: C 72.7; H 10.2%.

(c) Preparation of 2,4,4-trimethyl-2-cyclohexane-1-carboxylic acid

Methyl 2,4,4-trimethyl-2-cyclohexane-1-carboxylate (0.5 g; 2.75 m. moles) was added to 6% aqueous sodium hydroxide solution (5 ml) and the mixture stirred and heated at 50° C. for a period of 6½ hours. The homogeneous solution was washed twice with light petroleum (b.p. 60°–80° C.), acidified with dilute hydrochloric acid and extracted three times with ether. The dried (MgSO$_4$) extract was evaporated to give 2,4,4-trimethyl-2-cyclohexane-1-carboxylic acid (0.391 g; 88%) as an oil which failed to crystallise (N.M.R.: δ0.93 (s,3,CH$_3$—C—CH$_3$), 0.98 (s,3,CH$_3$—C—CH$_3$), 1.71 (d, J=~1 Hz., 3,C=C—CH$_3$), 5.21–5.38 (m,1,C=CH)). A sample of the material was reconverted into the methyl ester by treatment with diazomethane and shown to be pure by G.L.C. and T.L.C. A further sample was converted, in high yield, into the S-benzyl-thiuronium derivative, m.p. 140° C.

Analysis: Calculated for C$_{18}$H$_{26}$N$_2$O$_2$S: C 64.6; H 7.8; N 8.4; S 9.6%. Found: C 64.5; H 7.8; N 8.1; S 9.7%.

(d) Preparation of methyl 2,4,4-trimethyl-1-cyclohexene-1-carboxylate

Methyl 2,4,4-trimethyl-2-cyclohexene-1-carboxylate (0.91 g; 5.0 m. moles) was dissolved in a solution of sodium (0.12 g; 5.2 m. moles) in methanol (10 ml) and the mixture was heated at 50° C. for a period of 76 hours. The solution was diluted with dilute hydrochloric acid, extracted three times with ether and the combined extracts washed with aqueous sodium carbonate. The dried (MgSO$_4$) extract was evaporated and the residue distilled to give methyl 2,4,4-trimethyl-1-cyclohexane-1-carboxylate (0.8 g 89%), b.p. 104°–106° C./10 mm (N.M.R. : δ0.9 (s,6,CH$_3$—C—CH$_3$), 1.95 (b,3,C=C—CH$_3$), 3.61 (s,3,OCH$_3$)).

(e) Preparation of 2,4,4-trimethyl-1-cyclohexene-1-carboxylic acid

Methyl 2,4,4-trimethyl-1-cyclohexene-1-carboxylate (0.5 g; 2.75 m. moles) was added to 8% aqueous sodium hydroxide solution (5 ml) and the mixture was heated under reflux for a period of 24 hours. The solution was washed with light petroleum (b.p. 60°–80° C.), acidified with dilute hydrochloric acid and extracted three times with ether. The combined extracts were dried (MgSO$_4$)

and evaporated to give a crystalline product (0.373 g; 82%) which was recrystallized from aqueous methanol to give 2,4,4-trimethyl-1-cyclohexene-1-carboxylic acid (0.3 g; 66%), m.p. 108°-110° C., (N.M.R.: δ0.92 (s,6,CH$_3$—C—CH$_3$), 2.05 (b,3,C=C—CH$_3$)).

EXAMPLE 15

A stream of dry oxygen was passed through a stirred solution (heated at 30°-35° C.) of 1-(4-ethoxyphenyl)-2,2,2-trichloroethanol (5.86 g; 21.5 m. moles) in methanol (30 ml) and a solution of cupric chloride dihydrate (0.196 g; 1.12 m. moles) and catechol (0.3167 g; 2.88 m. moles) in methanol (30 ml) in which sodium (1.72 g; 74.78 m. moles) had been dissolved was added portionwise over a period of 6¾ hours.

The reaction mixture was diluted with water (100 ml), acidified with hydrochloric acid and extracted with ether (3×75 ml). The combined extracts were washed with saturated aqueous sodium carbonate (50 ml), water (50 ml) and dried (MgSO$_4$). Ether was removed by evaporation and the residue was flash distilled to give crude product (3.68 g).

The crude product was analyzed by G.L.C. using standard solutions of both ester and starting material for calibration purposes. The results indicated a 44% conversion of starting material and a 24.5% yield of methyl 4-ethoxybenzoate based on unrecovered starting material.

What is claimed is:

1. A process for preparing carboxylic acids and/or esters from 1-substituted 2,2,2-trihaloethanols or acylated derivatives thereof which comprises reacting the 1-substituted-2,2,2-trihaloethanol or acylated derivative with molecular oxygen in the presence of a catalyst comprising copper complexed with at least one molecule of a ligand containing 1,10-phenanthroline or 2,2'-bipyridyl; thereby converting the

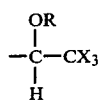

moiety of 1-substituted 2,2,2-trihaloethanol, wherein X represents halogen and R is hydrogen or an acyl group to a carboxylic acid and/or ester grouping of the formula

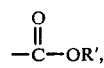

wherein R' represents hydrogen or alkyl of 1 to 6 carbon atoms; said reaction being carried out in an alcohol or aqueous alcohol solvent which optionally contains alkali metal hydroxide or alkoxide and in which the alcohol is of the formula R" OH, wherein R" is alkyl of 1 to 6 carbon atoms, said alcohol also functioning as the alcohol reactant source for the formation of carboxylic acid esters in the reaction.

2. The process according to claim 1, wherein the alcohol solvent contains alkali metal alkoxide.

3. The process according to claim 2, wherein the alkali metal alkoxide containing alcohol solvent is methanolic sodium methoxide or ethanolic sodium ethoxide.

4. The process according to claim 3 wherein the 1-substituted 2,2,2-trihaloethanol reactant is one in which the

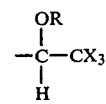

moiety is linked to an organic group selected from the class consisting of alkyl, alkenyl, cycloalkyl, cycloalkenyl or aryl, each optionally substituted with hydroxyl or alkoxy groups.

5. The process according to claim 3, wherein X is chloride.

6. The process according to claim 5, wherein the 1-substituted, 2,2,2-trichloroethanol is 1-(4-methoxyphenyl)-2,2,2-trichloroethanol.

7. The process according to claim 5, wherein the 1-substituted, 2,2,2-trichloroethanol is 1-(4-hydroxyphenyl)-2,2,2-trichloroethanol.

8. The process according to claim 5, wherein the 1-substituted, 2,2,2-trichloroethanol is 1-(2-cyclohexen-1-yl)-2,2,2-trichloroethanol.

9. The process according to claim 5, wherein the 1-substituted, 2,2,2-trichloroethanol is 1-(2-cyclododecen-1-yl)-2,2,2-trichloroethanol.

10. The process according to claim 5, wherein the 1-substituted, 2,2,2-trichloroethanol is 1-cyclohexyl-2,2,2-trichloroethanol.

11. The process according to claim 5, wherein the 1-substituted, 2,2,2-trichloroethanol is 1,1,1-trichloro-3-methyl-4-penten-2-ol.

12. The process according to claim 1, wherein said reaction is carried out in an alcohol solvent.

* * * * *